United States Patent
Barias et al.

(10) Patent No.: US 11,623,906 B2
(45) Date of Patent: Apr. 11, 2023

(54) OXYGEN STRIPPING IN ETHERIFICATION, ETHERS DECOMPOSITION AND ISOOCTENE PRODUCTION

(71) Applicant: LUMMUS TECHNOLOGY LLC, Bloomfield, NJ (US)

(72) Inventors: Rosette Barias, Spring, TX (US); Maurice Korpelshoek, Sk Gouda (NL); Michael Jon Scott, Houston, TX (US); Eric Arthur Schwarz, Bloomfield, NJ (US); Shahid Jamal, Bloomfield, NJ (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 58 days.

(21) Appl. No.: 17/400,318

(22) Filed: Aug. 12, 2021

(65) Prior Publication Data
US 2022/0048843 A1    Feb. 17, 2022

Related U.S. Application Data

(60) Provisional application No. 63/066,551, filed on Aug. 17, 2020.

(51) Int. Cl.
| | | |
|---|---|---|
| *C07C 41/06* | (2006.01) | |
| *C07C 41/42* | (2006.01) | |
| *B01D 3/00* | (2006.01) | |
| *B01J 8/02* | (2006.01) | |
| *B01J 8/00* | (2006.01) | |
| *B01D 11/04* | (2006.01) | |
| *B01D 5/00* | (2006.01) | |
| *B01D 19/00* | (2006.01) | |
| *B01D 3/14* | (2006.01) | |

(52) U.S. Cl.
CPC .............. *C07C 41/06* (2013.01); *B01D 3/009* (2013.01); *B01D 3/143* (2013.01); *B01D 5/006* (2013.01); *B01D 11/0492* (2013.01); *B01D 19/00* (2013.01); *B01J 8/003* (2013.01); *B01J 8/025* (2013.01); *B01J 8/0292* (2013.01); *C07C 41/42* (2013.01); *B01J 2208/027* (2013.01)

(58) Field of Classification Search
CPC .......... C07C 41/06; C07C 41/42; B01D 3/009
See application file for complete search history.

(56) References Cited

U.S. PATENT DOCUMENTS

| | | |
|---|---|---|
| 4,066,514 A | 1/1978 | Fowler |
| 7,138,557 B2 | 11/2006 | Senetar |
| 7,678,235 B2 | 3/2010 | Deep et al. |
| 2002/0017480 A1 | 2/2002 | Emmrich et al. |
| 2010/0101415 A1 | 4/2010 | Find et al. |
| 2018/0194644 A1 | 7/2018 | Fischer et al. |
| 2020/0048160 A1 | 2/2020 | Senetar |

FOREIGN PATENT DOCUMENTS

| | | |
|---|---|---|
| CN | 1391499 A | 1/2003 |
| CN | 103998381 A | 8/2014 |
| TW | 200720194 A | 6/2007 |

OTHER PUBLICATIONS

International Search Report issued in International Application No. PCT/US2021/045653 dated Dec. 3, 2021 (3 pages).
Written Opinion issued in International Application No. PCT/US2021/045653 dated Dec. 3, 2021 (4 pages).
Office Action and Search Report issued in corresponding TW Application No. 110129993 dated Apr. 8, 2022 (6 pages).

*Primary Examiner* — Sikarl A Witherspoon
(74) *Attorney, Agent, or Firm* — Osha Bergman Watanabe & Burton LLP

(57) ABSTRACT

A process for supplying deaerated water to a chemical plant that includes a distillation column for separating a reaction effluent comprising water and a product. The process includes inventorying the distillation column with aerated water (water having an oxygen content of greater than 50 ppbw, such as greater than 1 ppmw). The aerated water in the distillation column may then be distilled to produce an oxygen-containing overheads and a bottoms fraction comprising deaerated water. The deaerated water in the bottoms fraction ma be transported to an upstream or a downstream unit operation, and utilizing the deaerated water in the upstream or downstream unit operation. The reaction effluent is fed to the distillation column, transitioning the distillation column from separating oxygen from water to operations for separating the product from the water.

14 Claims, 3 Drawing Sheets

OXYGEN STRIPPING IN ETHERIFICATION, ETHERS DECOMPOSITION AND ISOOCTENE PRODUCTION

BACKGROUND

Oxygen ingress into various chemical operations can be problematic. In addition to formation of undesired byproducts, the oxygen may also result in corrosion of piping and other equipment. To deal with the expected corrosion, typically the metallurgy associated with the plants is upgraded, adding capital expense.

Oxygen ingress into the chemical plant may come from a variety of sources, including water supplies. To prevent oxygen ingress, many plants include a water deaeration system. Unfortunately, the chemical injections used with such deaeration systems have been found to impact the performance of various downstream systems. As one example, deaeration chemicals may negatively impact the performance of etherification catalysts such as may be used in a process for producing methyl tert-butyl ether (MTBE).

SUMMARY

Embodiments herein provide systems and methods to avoid the negative effects of oxygen ingress and deaeration chemicals.

In one aspect, embodiments herein relate to a process for supplying deaerated water to a chemical plant that includes a distillation column for separating a reaction effluent comprising water and a product. The process includes inventorying the distillation column with aerated water (water having an oxygen content of greater than 50 ppbw, such as greater than 1 ppmw) (ppbw=parts per billion by weight; ppm=parts per million by weight). The aerated water in the distillation column may then be distilled to produce an oxygen-containing overheads and a bottoms fraction comprising deaerated water. The deaerated water in the bottoms fraction ma be transported to an upstream or a downstream unit operation, and utilizing the deaerated water in the upstream or downstream unit operation. The reaction effluent is fed to the distillation column, transitioning the distillation column from separating oxygen from water to operations for separating the product from the water.

In another aspect, embodiments herein relate to a method for starting up a system for producing methyl tert-butyl ether (MTBE). The system for producing MTBE may include: an etherification reactor, a catalytic distillation etherification reactor, an extraction column, and a distillation column, among other components. Flow lines may be provided for feeding methanol and a mixed C4 stream, comprising isobutylene and other olefinic and/or paraffinic C4s, to the etherification reactor, reacting the isobutylene and methanol to produce a crude MTBE effluent comprising MTBE, unreacted isobutylene, unreacted methanol, and the other olefinic and/or paraffinic C4s. The catalytic distillation reactor may be configured for concurrently (i) reacting the unreacted isobutylene and methanol to form additional MTBE, and (ii) separating the crude MTBE to recover a bottoms fraction comprising the MTBE and an overheads fraction comprising methanol and the other olefinic and/or paraffinic C4s. The extraction column may be configured for extracting the unreacted methanol with water, producing a C4 raffinate fraction comprising the other olefinic and/or paraffinic C4s, and an extract fraction comprising water and methanol. Further, the distillation column may be configured for separating the extract fraction to recover an overheads fraction comprising methanol and a bottoms fraction comprising water. The method for starting up the system for producing MTBE may include inventorying the distillation column with aerated water (water having an oxygen content of greater than 50 ppbw, such as greater than 1 ppmw), distilling the aerated water in the distillation column to produce an oxygen-containing overheads and a bottoms fraction comprising deaerated water having less than 15 ppbw oxygen, and transporting the deaerated water in the bottoms fraction to the extraction column. The inventorying, distilling, and transporting are repeated until the extraction column and distillation column are fully inventoried with deaerated water. Subsequently, the process includes starting up the reactor and the catalytic distillation reactor, and feeding the overheads fraction comprising the methanol and the other olefinic and/or paraffinic C4s to the extraction column, transitioning the extraction column to producing the C4 raffinate fraction and the extract fraction comprising water and methanol. The extract fraction is fed to the distillation column, transitioning the distillation column to separating the methanol from the water.

In some embodiments, the repeating comprises conducting the inventorying, distilling, and transporting continuously, recirculating water from the extraction column to the distillation column until the water is deaerated.

In other embodiments, the repeating comprises conducting the inventorying, distilling, and transporting batchwise in the distillation column, transporting batches of deaerated water to inventory the extraction column. When operating batchwise, the method may also include accumulating a volume of deaerated water in a sump of the distillation column.

In various embodiments, the distillation column may also include an overheads condensation system. The method further includes recovering an overheads fraction from the distillation column, the overheads fraction comprising water vapor and oxygen, cooling the overheads fraction to condense at least a portion of the water, forming a cooled overhead fraction, feeding the cooled overhead fraction to an overhead drum, accumulating a liquid water fraction and a vapor fraction comprising the oxygen, withdrawing the vapor fraction from the overhead drum, and feeding the liquid water fraction to the distillation column as a reflux. The liquid water fraction may be fed to the distillation column as a total reflux. In some embodiments, nitrogen may be fed to the overhead drum, wherein the vapor fraction comprises nitrogen and oxygen. Various embodiments also include measuring an oxygen content of the bottoms fraction.

DETAILED DESCRIPTION

Figure 1:
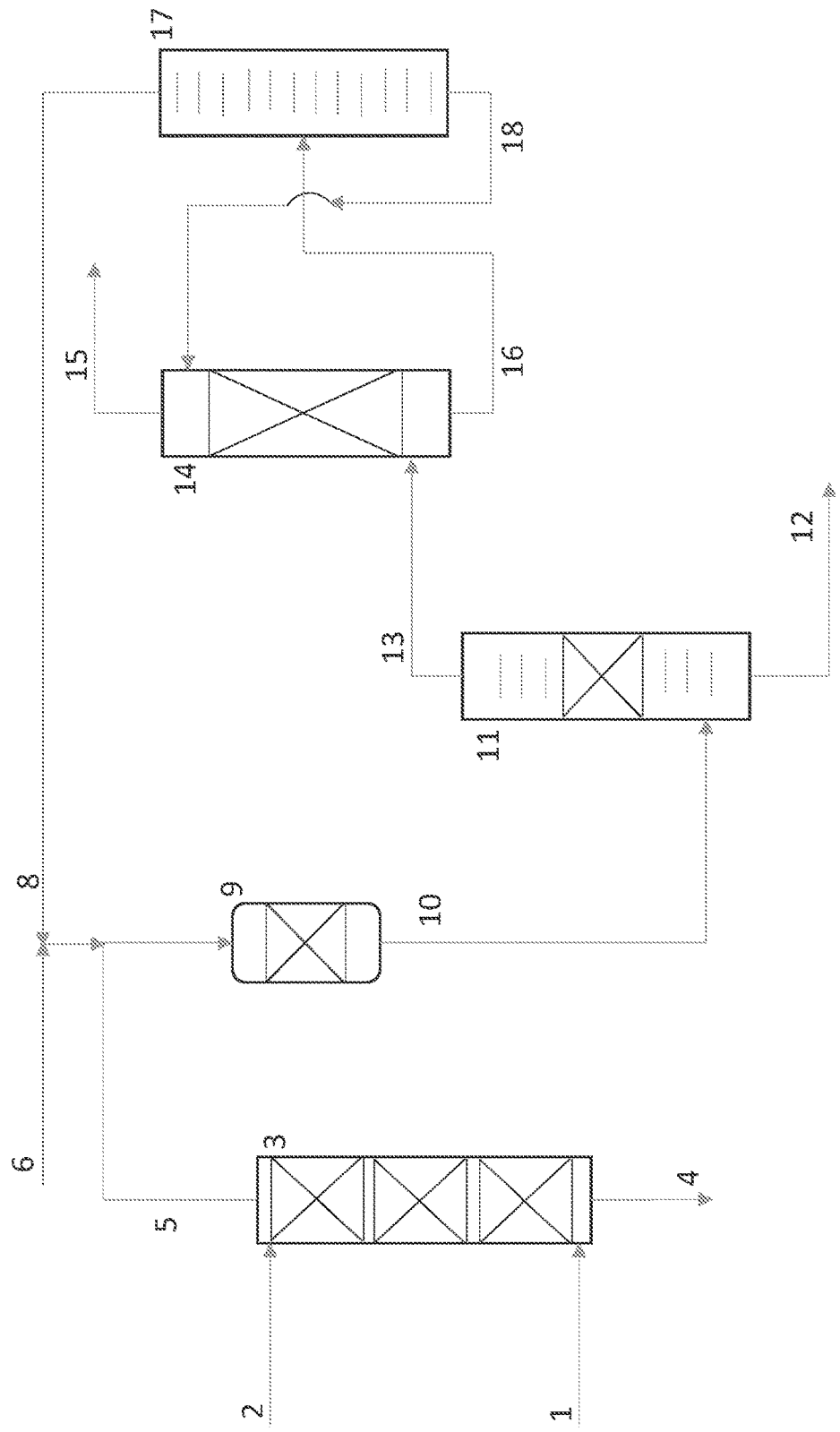
FIG. 1 is a simplified process flow diagram of a process for producing methyl tert-butyl ether (MTBE) according to embodiments herein.

Deaerated water is needed in various chemical processes. As one example, deaerated water may be used in a process for producing methyl tert-butyl ether (MTBE). As another example, deaerated water may be required in a process for converting MTBE to isooctene. Embodiments herein are directed toward methods and systems for efficiently providing deaerated water to these and other various chemical processes that may require a deaerated water supply.

Processes that may benefit from embodiments herein may include those that have a distillation column typically used for separating a mixture, such as a feed stream or reaction effluent, that includes water and one or more of a product, byproduct, intermediate, or recycle component. As opposed to a chemical deaeration system, embodiments herein utilize the distillation column to produce deaerated water for supply to and use in the chemical process system.

Generating a deaerated water supply may be performed during startup of the overall chemical process and may include an initial inventory of the distillation column with aerated water. As used herein, aerated water may refer to water having an oxygen content of greater than 50 ppbw. Some water supplies may contain, for example, 10 ppmw oxygen or greater.

Following the inventory of the distillation column, the aerated water in the distillation column may be distilled to produce an oxygen-containing overheads and a bottoms fraction comprised of deaerated water. The deaerated water may contain less than 15 ppbw oxygen, such as from less than 1 ppbw to no more than 10 ppbw oxygen.

The deaerated water in the bottoms fraction may then be transported to an upstream or a downstream unit operation. As the startup continues and normal operations of the chemical plant commence, the process may include utilizing the deaerated water in the upstream or downstream unit operation, the operations further producing the mixture, including water and one or more of a product, byproduct, intermediate, or recycle component, which is fed to the distillation column. The distillation column may then be transitioned to normal operations, separating the water from the one or more of a product, byproduct, intermediate, or recycle component.

The distillation column may include an overheads condensation system in some embodiments. In such embodiments, the process may further include, during startup, to generate the deaerated water supply, recovering an overheads fraction from the distillation column. The overheads fraction recovered from the distillation column may contain water vapor and oxygen. The overheads fraction may then be cooled to condense at least a portion of the water, forming a cooled overhead fraction, which may be fed to an overhead drum. In the overhead drum, a liquid water fraction may be separated from a vapor fraction, including the oxygen, and a level of liquid water may be accumulated. The vapor fraction comprising the oxygen may be withdrawn from the overhead drum through the vent. The liquid water fraction may be fed to the distillation column as a reflux. The withdrawn vapor fraction thus removes oxygen from the water circulating through the distillation column, reducing the oxygen content in the water, including the water at the bottom of the distillation column or accumulating in a sump of the distillation column.

In some embodiments, a nitrogen feed may be supplied to the overhead drum. In such embodiments, the vapor fraction withdrawn from the overhead drum may include both nitrogen and oxygen. The nitrogen may act as a sweep gas to remove the oxygen. Further, the nitrogen may be used to maintain a pressure greater than atmospheric pressure within the distillation column, during production of deaerated water, during normal operations, or both.

To ensure that the water is sufficiently deaerated prior to supply to or use in the upstream or downstream unit operations, embodiments herein may include measuring an oxygen content of the bottoms fraction. The water at the bottom of the distillation column circulating through a reboiler of the distillation system, or accumulating/circulating from a sump of the distillation system may be sampled to measure an oxygen content of the water. Embodiments herein further contemplate on-line measurement of the water oxygen content at various points in the system to verify the water is deaerated sufficiently.

As described above, embodiments herein provide for use of process equipment for the provision of an initial startup quantity of deaerated water. Fresh or make-up water may also be supplied to the distillation column, deaerating the fresh or make-up water prior to usage. Where make-up deaerated water may be required for the upstream or downstream unit operations, a volume of the sump may be oversized as compared to that needed for typical distillation operation to allow for influx and processing of the fresh or make-up water.

The above described startup procedures to provide deaerated water may be used advantageously in a system for producing MTBE, for example. The process of etherification may include, for example, a water wash system as a form of feed pretreatment as well as the extraction of alcohol using water. The water specification for such a system may be deaerated water, and thus the process to provide deaerated water described above may be used to inventory deaerated water in the system.

A simplified process flow diagram of a system for producing MTBE is illustrated in FIG. 1. A mixed stream of C4s containing isobutene may be fed via line 1. If desired or necessary, the mixed C4s may be washed with water 2 in water wash column 3 to remove any undesired impurities. The wash water may be recovered via flow stream 4 and the washed C4s may be recovered via flow stream 5.

The washed C4s 5 and methanol 6 may be combined and fed to a down flow fixed bed reactor 9 which contains a fixed bed of etherification catalyst, such as an acid cation exchange resin. In the reactor 9, most of the isobutene may be reacted with methanol to form the MTBE.

The effluent from the down flow fixed bed reactor containing MTBE, methanol, and unreacted C4s is recovered via flow line 10 and fed into the lower portion of a distillation column reactor 11. The lower portion of the distillation column reactor contains standard distillation structure such as inert packing, sieve trays or bubble cap trays. In this section, the distillation section, the MTBE is recovered and taken as bottoms via line 12.

The upper portion of the distillation column reactor contains the catalytic distillation structure and additional conventional distillation structure may be placed above the distillation reaction zone. The unreacted methanol and C4s are boiled up into the distillation reaction zone 22 where most of the remainder of the isobutene is converted to MTBE which is simultaneously distilled down and finally removed as product 12. Unreacted methanol, C4s and inerts are taken overhead via flow line 13 and passed to methanol extraction column 14.

In methanol extraction column 14, the mixture of methanol and C4s is contacted with an extractant, such as water or a mixture containing water, to absorb the methanol. A C4 raffinate, depleted in isobutylene, may be recovered from the methanol extraction column as an overheads 15. The extractant, including methanol and water, may be recovered via bottoms stream 15 and fed to methanol recovery column 17.

Methanol recovery column 17 may be used to separate the methanol from the extractant. The methanol may be recovered as an overheads fraction 8, which may be recycled to the etherification reactor 9, for example, for continued conversion of methanol. The extractant may be recovered from the methanol recovery column as a bottoms fraction 18, which may be recycled for use as the extractant in the methanol extraction column.

While described with respect to a single methanol recovery column 17, embodiments using more complex methods to recover a high purity methanol product stream are also envisioned. Such methods may include multiple distillation columns, divided wall distillation columns and other systems to separate methanol from water.

As described with respect to FIG. 1, water is used in the water wash column 3, methanol extraction column 14, and methanol recovery column 17. The above described startup procedures may thus be used advantageously to inventory the system with deaerated water.

Figure 2:
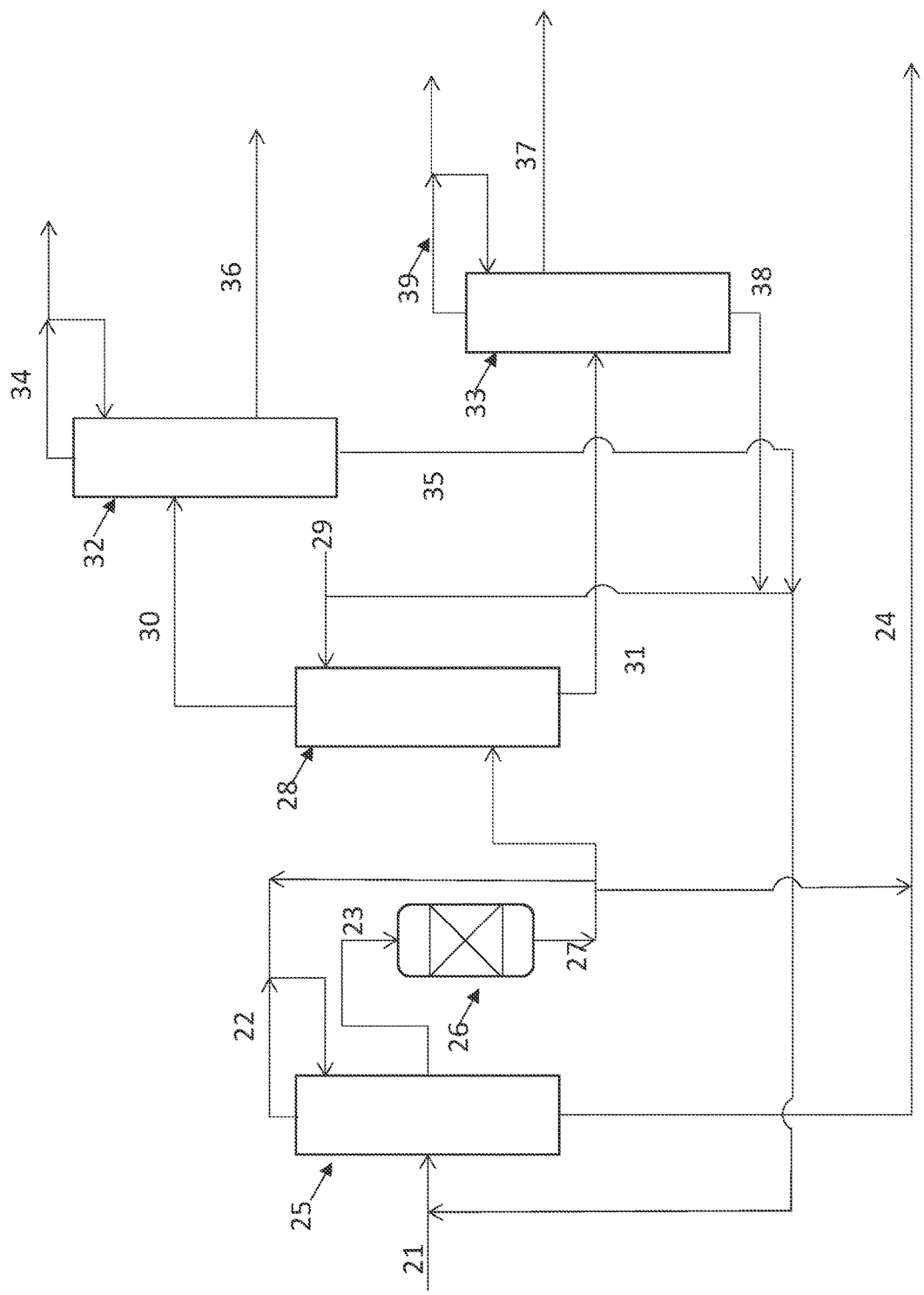
FIG. 2 is a simplified process flow diagram of a process for producing isobutylene and/or isooctene according to embodiments herein.

The above described startup procedures to provide deaerated water may also be used advantageously in a system for producing high purity isobutylene or isooctene from MTBE, for example. Isobutylene in the mixed butenes stream may be reacted with an alcohol, such as methanol, to form MTBE, as described above. After separation from the normal butenes, the MTBE may then be dissociated to form isobutylene and methanol, allowing recovery of a high purity isobutylene stream. Such a step may also allow the separation of 1-butene from 2-butene in the remaining unreacted C4s. The high purity isobutylene stream may then be selectively dimerized, to form isooctene, for example, or may be trimerized, oligomerized or otherwise used as a feedstock in various chemical processes. A simplified process flow diagram for converting MTBE to high purity isobutylene or isooctene is illustrated in FIG. 2.

Crude MTBE 21 is introduced into a divided wall fractionation column 25. Crude MTBE 21 may be obtained, as described with respect to FIG. 1, from isobutenic C4 olefin mixtures, such as from the C4 cut from steam crackers or FCC units. The crude MTBE may also include methanol, secondary butyl alcohol (SBA), tert-butyl alcohol (TBA), 2-methoxybutane (MSBE), diisobutene, tertiary amyl methyl ether (TAME) and other high boiling point components.

In some embodiments, the crude MTBE stream 21 may include a 94-97 wt % MTBE stream, such as a 95.9 wt % MTBE. The crude MTBE stream 21 may also contain small amounts of highly unsaturated compounds such as 1,3-butadiene, trans-1,3-pentadiene, cis-1,3-pentadiene, 2-methyl-1,3-butadiene, and others. The feed stream may additionally be comprised of crude MTBE provided from an upstream etherification reaction zone and a supplemental MTBE feed stream. Such supplemental MTBE feed streams may come from a separate facility, OSBL, an upstream separation system, or other sources.

The MTBE stream 21 can be introduced at an intermediate point in the column 25. A light hydrocarbon stream 22 can be withdrawn as an overheads from the column 25 and a side-draw stream 23 can also be withdrawn from column 25. A portion of the light hydrocarbon stream 22 may be recycled to the top of the column 25 as a reflux. The light hydrocarbon stream 22 may be a mixture of MTBE, methanol, water, and highly unsaturated compounds. The side-draw stream may be an MTBE stream of increased purity as compared to the MTBE feed stream 21. The side stream may further include one or more impurities present in the feed stream. A heavy hydrocarbon stream 24 can be withdrawn as a bottoms fraction from the divided wall column 25. The heavy hydrocarbon 24 may be a mixture of MTBE, tert-butyl alcohol (TBA), 2-methoxybutane (MSBE) and higher olefins.

The fractionation column 25 may operate at temperatures ranging from about 45° C. to about 130° C. and pressures ranging from about 0.1 to about 5 barg. The purification of MTBE 21 provides the sidestream (MTBE) 23 having a composition such as about 99.5 wt % MTBE or greater, such as 99.8 wt % MTBE or 99.9 wt % MTBE. The MTBE side stream may be produced by fractional distillation in the fraction system 25, separating the MTBE 21 into the light hydrocarbons 22 comprising MTBE, methanol, water and other low boiling components, and the heavy hydrocarbons 24 comprising butene oligomers, TBA, and other high boiling components, while withdrawing the high purity MTBE sidestream 23.

To produce isobutene, the MTBE sidestream 23 may be sent to a reactor 26 to produce isobutene. The reactor 26 dissociates the high purity MTBE 23 and produces a raw isobutene stream 27 comprised of isobutene, methanol and unreacted MTBE. In some embodiments, the reactor 26 includes a fixed bed operating at reaction bed temperatures ranging from about 90° C. to about 160° C., in other embodiments from about 120° C. to about 150° C. The high purity MTBE 23 may be fed at an inlet temperature of about 110° C. to about 150° C. in some embodiments, about 115° C. to about 145° C. in other embodiments. The reactor 26 may have an LHSV (liquid hourly space velocity) ranging from about 7 to about 35, or from about 10 to about 30, or from about 14 to about 25. The reactor 26 may have a pressure drop through said fixed bed in the range of about 0.5 to about 50 psig and at a reaction pressure ranging from about 0.5 to about 4 atmospheres.

The raw isobutene stream 27 is sent for product purification. The raw isobutene 27 may be sent to an extraction column 28 to extract methanol and unreacted MTBE from isobutene. The extraction column 28 uses an extractant 29 fed in a countercurrent fashion to the raw isobutene 7 thereby producing a washed reactor effluent 30 as an overhead and a bottoms product 31. The washed reactor effluent 30, which may include isobutene, MTBE, and residual light components, may be fed to an isobutene fractionation system 32 and the bottoms product 31, which may include water, methanol, MTBE, and residual heavy components, may be fed to a methanol fractionation system 33. The extractant 29 may be water or another suitable extractant useful to separate methanol from isobutene. Fresh extractant 29 may be fed to the extraction column 28. However, when water is used as the extractant, it may be beneficial to feed make-up or fresh water to the methanol fractionation system 33, so as to deaerate the added water within the fractionation system prior to use upstream in the extraction column or elsewhere in the process.

In various embodiments, at least a portion of the raw isobutene 27 may be recycled to the first fraction system 25 as additional reflux, collected as product, and/or combined with the heavy hydrocarbons 24 and sent offsite as byproduct.

To recover the isobutene, the method may include introducing the washed reactor effluent 30 to an isobutene fractionation system 32. The washed reactor effluent 30 may be introduced at an intermediate point of the isobutene fractionation column 32. A light ends overhead 34 can be withdrawn from the isobutene fractionation column 32 at or proximal the upper end thereof and may be vented or recycled to the isobutene fractionation system 32 as reflux.

A side-stream of high purity isobutene 36 can be withdrawn from an intermediate point of the isobutene fractionation column 32, which may be used in downstream processes, such as for dimerization to isooctene, or may be recovered as a product and sent offsite. Such high purity isobutene stream may have a purity of 95 wt %, 97 wt %, 98 wt %, 99 wt %, 99.5 wt %, 99.6 wt %, 99.7 wt %, 99.8 wt %, or even 99.85 wt % isobutene. The isobutene column 32 may also produce a bottom product 35, which may be a mixture of isobutene, MTBE and/or water which may be recycled to fractionation system 25. The isobutene column 32 may operate at temperatures ranging from about 45° C. to about 150° C. and pressures ranging from about 3 to about 15 barg.

To recover/purify a methanol product stream, the bottoms product 31 from the extraction column 28 may be fed to an intermediate point of the methanol fractionation system 33. The methanol fractionation system may a series of fractionation columns such a methanol toppings column followed by a methanol bottoms bottom column, or may be a divided wall column. The methanol fraction system 33 may provide a high purity methanol product 37 withdrawn as a side-stream from an intermediate point of the methanol column 33, a bottoms stream 38, and an overhead stream 39. The light overhead stream 39 may comprise methanol and other light components and may be vented or recycled to the methanol fractionation system 33 as reflux. The bottoms 38 may include water, TBA, MTBE and/or methanol. The bottoms 38 may be recycled to either the extraction column 28 or the fractionation system 25. The methanol column 33 may operate at temperatures ranging from about 45° C. to about 180° C. and pressures ranging from about 01 to about 5 barg.

As illustrated and described with respect to both FIG. 1 and FIG. 2, each system may utilize a deaerated water supply and each system includes a distillation column for separating water from a hydrocarbon (methanol fractionation system 17 in FIG. 1; methanol fractionation system 33 in FIG. 2). Startup procedures for the respective systems may thus provide deaerated water as may be needed throughout the system or for select portions thereof utilizing the distillation column typically used for separating water from the hydrocarbon during normal operations.

Figure 3:
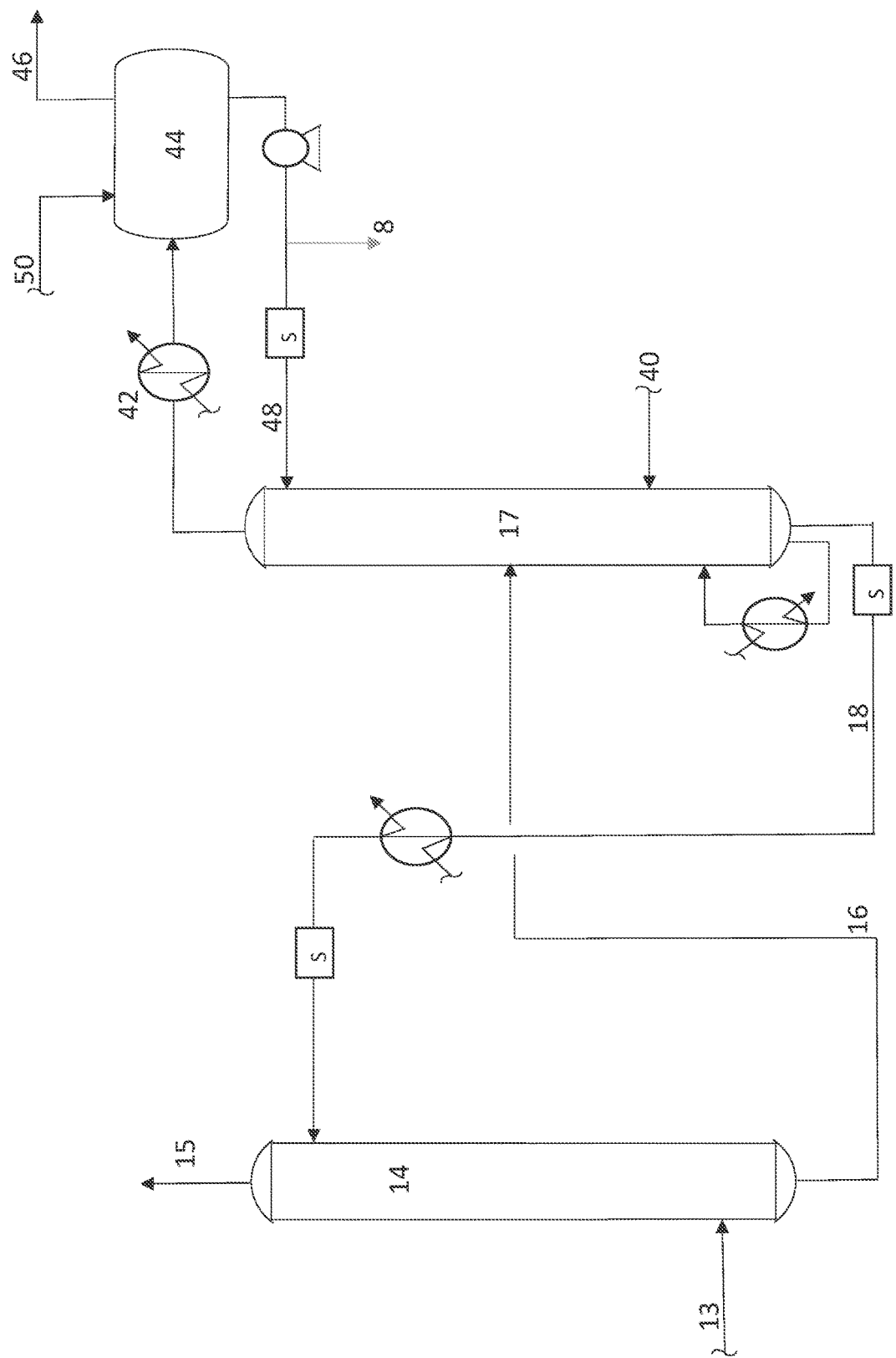
FIG. 3 is a simplified process flow diagram of an extraction plus distillation system useful in processes such as illustrated in FIG. 1 and FIG. 2.

Referring now to FIG. 3, a simplified diagram of the extraction column 14 and distillation column 17 used in the process to produce MTBE is illustrated. Prior to startup of the reactor section, the alcohol recovery column 17 may first be inventoried with demineralized water via water feed line 40. Demineralized water as commonly available may contain, for example, 10 ppmw oxygen, which is much higher than desired. The sump (bottoms collection area of the column) may be inventoried, for example, to an 80% level with the demineralized water. At this point, the tower is ready for startup with steam to the reboiler, etc.

As water starts to distill, the overhead condenser 42 is also commissioned. During this time, when water starts to condense overhead, fresh demineralized water is fed continuously to the sump to maintain liquid level. Also at this point, the water accumulates in the overhead drum 44. The vent valve (not illustrated) along the vent line 46 may be opened to vent the oxygen and other vapors from the drum. The vent line 46, which is normally connected to the flare, may have another line with a discharge to a safe location, including to the atmosphere, as the vapor being vented is only water vapor and oxygen at this time. The vent valve is opened gradually as the water in the drum starts to accumulate (condense). When the water in drum 44 reaches a sufficient level, such as about 30%, the reflux pump may then start on minimum flow. As level continues to build up in the drum 44 and while maintaining the sump level of the column 17, the reflux valve to the column is then opened to start a total reflux operation, the reflux being fed via flow line 48.

As the deaeration operation continues, the vent valve from the drum is kept partially open with the overhead pressure maintained at about 1 barg. Pressure in the column may be maintained, and oxygen may be swept from the system, for example, via introduction of nitrogen via flow line 50.

After a period of time distilling the water, which may be from 20 or 30 minutes to a couple hours of operation, an initial water sample may be taken to determine the level of oxygen remaining in the water. Water samples may be taken, for example, from the overheads system, such as via flow line 48, or from a bottoms line, such as water circulating through the reboiler or from a bottoms line 18. The deaeration of the water may continue until the oxygen specification for the water is met. Once the oxygen spec in the water is achieved, the steam to the reboiler may be reduced and the bottoms section of the alcohol recovery column may be opened to send the deaerated water to the extraction tower 14 until the liquid level in the alcohol recovery column is at its lowest level. When the liquid level in the alcohol recovery column is at its lowest level, the bottoms valve may be closed to stop the flow of stripped water to the extraction tower 14. The steps may be repeated until the operating level of deaerated water in the extraction tower and the alcohol recovery column are achieved.

As described with respect to FIG. 3, the water deaeration process may be conducted batchwise to inventory the extraction column and the distillation column with deaerated water. Embodiments herein further contemplate inventorying both the extraction column and the distillation column with water and then deaerating the water while circulating water through extraction column 14 and distilling water in column 17. In such embodiments, oxygen may be vented by one or both of flow lines 15 and 46.

The same idea in oxygen stripping is deemed applicable for any continuous water user within the etherification process. For a continuous water user, such as the water wash column, the sump of the alcohol recovery column may be designed with a bigger surge volume to provide sufficient inventory. At this point of the operation, the venting process is continuous with nitrogen used as a stripping media.

Various processes may include multiple water extraction columns. For example, a combined process converting mixed C4s to MTBE and then converting the MTBE to high purity isobutylene may have two extraction columns, one for the MTBE generation portion of the process, and one for the isobutylene (MTBE back cracking) portion of the process. Other processes may include two extraction columns for maintaining continuous operations. A single distillation column may be used to inventory each of these water users with deaerated water according to embodiments herein.

The above-described processes and startup procedures may also be used to provide deaerated water in various other processes, including those for the production of ethyl tertiary butyl ether, tertiary amyl methyl ether, tertiary amyl ethyl ether, mixed ethers, etherol, destruction of ethers to form olefins, and production of isooctene or other various processes that may include a water wash, water extraction or other unit operations in which a deaerated water supply is needed. Advantageously, embodiments herein provide the ability to deaerate water and supply water users within the plant without the added operating and capital expense of a dedicated deaeration system.

What is claimed as new and desired to be protected by Letters Patent is:

1. A process for supplying deaerated water to a chemical plant, wherein the chemical plant includes a distillation column for separating a reaction effluent comprising water and a product, the process comprising:
   inventorying the distillation column with aerated water having an oxygen content of greater than 50 ppbw;
   distilling the aerated water in the distillation column to produce an oxygen-containing overheads and a bottoms fraction comprising deaerated water;
   transporting the deaerated water in the bottoms fraction to an upstream or a downstream unit operation;
   utilizing the deaerated water in the upstream or downstream unit operation; and
   feeding the reaction effluent to the distillation column, transitioning the distillation column from separating oxygen from water to operations for separating the product from the water.

2. The process of claim 1, wherein the deaerated water comprises less than 15 ppbw oxygen.

3. The process of claim 1, wherein the deaerated water comprises from less than 1 ppbw to no more than 10 ppbw oxygen.

4. The process of claim 1, wherein the distillation column comprises an overheads condensation system, the process further comprising:
   recovering an overheads fraction from the distillation column, the overheads fraction comprising water vapor and oxygen;
   cooling the overheads fraction to condense at least a portion of the water, forming a cooled overhead fraction;
   feeding the cooled overhead fraction to an overhead drum, accumulating a liquid water fraction and a vapor fraction comprising the oxygen;
   withdrawing the vapor fraction from the overhead drum; and
   feeding the liquid water fraction to the distillation column as a reflux.

5. The process of claim 1, further comprising feeding nitrogen to the overhead drum, wherein the vapor fraction comprises nitrogen and oxygen.

6. The process of claim 1, further comprising measuring an oxygen content of the bottoms fraction.

7. A method for starting up a system for producing methyl tert-butyl ether (MTBE), wherein the system comprises:
   flow lines and a reactor, the flow lines configured for feeding methanol and a mixed C4 stream, comprising isobutylene and other olefinic and/or paraffinic C4s, and the reactor configured for reacting the isobutylene and methanol to produce a crude MTBE effluent comprising MTBE, unreacted isobutylene, unreacted methanol, and the other olefinic and/or paraffinic C4s;
   a catalytic distillation reactor for concurrently (i) reacting the unreacted isobutylene and methanol to form additional MTBE, and (ii) separating the crude MTBE to recover a bottoms fraction comprising the MTBE and an overheads fraction comprising methanol and the other olefinic and/or paraffinic C4s;
   an extraction column for extracting the unreacted methanol with water, producing a C4 raffinate fraction comprising the other olefinic and/or paraffinic C4s, and an extract fraction comprising water and methanol;
   a distillation column for separating the extract fraction to recover an overheads fraction comprising methanol and a bottoms fraction comprising water;
   the method comprising:
   inventorying the distillation column with aerated water, having an oxygen content of greater than 50 ppbw;
   distilling the aerated water in the distillation column to produce an oxygen-containing overheads and a bottoms fraction comprising deaerated water having less than 15 ppbw oxygen;
   transporting the deaerated water in the bottoms fraction to the extraction column;
   repeating the inventorying, distilling, and transporting until the extraction column and distillation column are fully inventoried with deaerated water; and
   starting up the reactor and the catalytic distillation reactor;
   feeding the overheads fraction comprising the methanol and the other olefinic and/or paraffinic C4s to the extraction column, transitioning the extraction column to producing the C4 raffinate fraction and the extract fraction comprising water and methanol;
   feeding the extract fraction to the distillation column, transitioning the distillation column to separating the methanol from the water.

8. The method of claim 7, wherein the repeating comprises conducting the inventorying, distilling, and transporting continuously, recirculating water from the extraction column to the distillation column until the water is deaerated.

9. The method of claim 7, wherein the repeating comprises conducting the inventorying, distilling, and transporting batchwise in the distillation column, transporting batches of deaerated water to inventory the extraction column.

10. The method of claim 9, further comprising accumulating a volume of deaerated water in a sump of the distillation column.

11. The method of claim 7, wherein the distillation column comprises an overheads condensation system, the method further comprising:
   recovering an overheads fraction from the distillation column, the overheads fraction comprising water vapor and oxygen;
   cooling the overheads fraction to condense at least a portion of the water, forming a cooled overhead fraction;
   feeding the cooled overhead fraction to an overhead drum, accumulating a liquid water fraction and a vapor fraction comprising the oxygen;
   withdrawing the vapor fraction from the overhead drum; and
   feeding the liquid water fraction to the distillation column as a reflux.

12. The method of claim 11, comprising feeding the liquid water fraction to the distillation column as a total reflux.

13. The method of claim 11, further comprising feeding nitrogen to the overhead drum, wherein the vapor fraction comprises nitrogen and oxygen.

14. The method of claim 11, further comprising measuring an oxygen content of the bottoms fraction.

* * * * *